(12) United States Patent
del Real Pena et al.

(10) Patent No.: US 12,311,140 B2
(45) Date of Patent: May 27, 2025

(54) MEDICAL FLUID LINE CONNECTION DEVICES

(71) Applicant: Fresenius Medical Care Holdings, Inc., Waltham, MA (US)

(72) Inventors: Diego Suarez del Real Pena, Mission, TX (US); Jose Eduardo Pena Martinez, Reynosa (MX)

(73) Assignee: Fresenius Medical Care Holdings, Inc., Waltham, MA (US)

(*) Notice: Subject to any disclaimer, the term of this patent is extended or adjusted under 35 U.S.C. 154(b) by 272 days.

(21) Appl. No.: 17/337,856

(22) Filed: Jun. 3, 2021

(65) Prior Publication Data

US 2022/0387774 A1 Dec. 8, 2022

(51) Int. Cl.
*A61M 39/10* (2006.01)
*A61M 1/16* (2006.01)
*A61M 1/28* (2006.01)
*A61M 1/34* (2006.01)
*A61M 39/28* (2006.01)

(52) U.S. Cl.
CPC .............. *A61M 39/10* (2013.01); *A61M 1/16* (2013.01); *A61M 1/28* (2013.01); *A61M 1/3413* (2013.01); *A61M 39/28* (2013.01); *A61M 2039/1061* (2013.01); *A61M 2207/00* (2013.01)

(58) Field of Classification Search
None
See application file for complete search history.

(56) References Cited

U.S. PATENT DOCUMENTS

| | | | | |
|---|---|---|---|---|
| 5,221,267 A | * | 6/1993 | Folden | A61M 1/28 604/905 |
| 5,836,619 A | * | 11/1998 | Shemesh | A61M 1/285 604/905 |
| 6,322,551 B1 | * | 11/2001 | Brugger | A61M 1/362262 604/905 |
| 6,739,628 B2 | * | 5/2004 | Kanner | F16L 9/00 604/905 |
| 7,544,191 B2 | | 6/2009 | Peluso et al. | |

(Continued)

FOREIGN PATENT DOCUMENTS

CN 112384184 2/2021
WO WO 95/12780 5/1995

OTHER PUBLICATIONS

[No Author Listed], "Instructions For Use: Cycler Drain Bag Set," Fresenius Medical Care, Dec. 21, 2018, 1 page.

(Continued)

*Primary Examiner* — Benjamin M Kurtz
(74) *Attorney, Agent, or Firm* — Fish & Richardson P.C.

(57) ABSTRACT

A medical fluid line connector includes a body defining a central opening extending therethrough, a first projection extending from a first portion of the body, and a second projection extending from a second portion of the body, the second projection being circumferentially and axially offset from the first projection. The first portion of the body and second portion of the body are configured to separate from one another in response to a threshold amount of force being applied to the first projection and the second projection to rotate the first portion of the body and second portion of the body relative to one another.

27 Claims, 10 Drawing Sheets

(56) References Cited

U.S. PATENT DOCUMENTS

| | | | |
|---|---|---|---|
| 8,926,571 B1 * | 1/2015 | Keith | A61M 5/16813 604/533 |
| 2002/0180207 A1 * | 12/2002 | Kanner | F16L 35/00 285/3 |
| 2021/0290486 A1 | 9/2021 | Ariagno et al. | |

OTHER PUBLICATIONS

Wright, "Customer Notification: Liberty Drain Set w/4-5 L BAGS (PN 026-20226) Design Change (PN 026-20226A)," Fresenius Medical Care, Sep. 2019, 1-3.

International Search Report and Written Opinion in International Appln. No. PCT/US2022/030286, dated Aug. 12, 2022, 32 pages.

International Preliminary Report on Patentability in International Appln. No. PCT/US2022/030286, mailed Dec. 14, 2023, 8 pages.

* cited by examiner

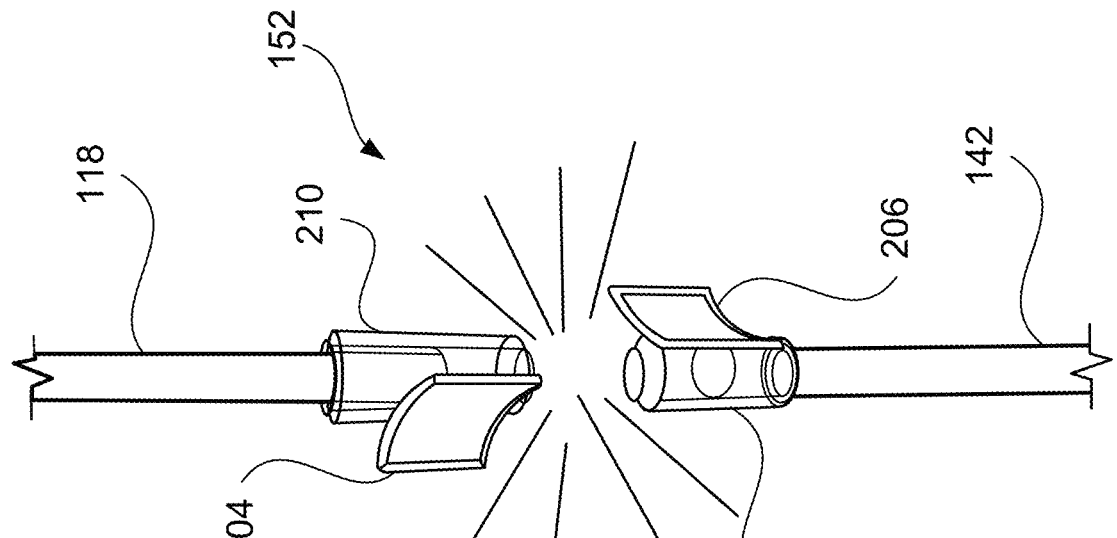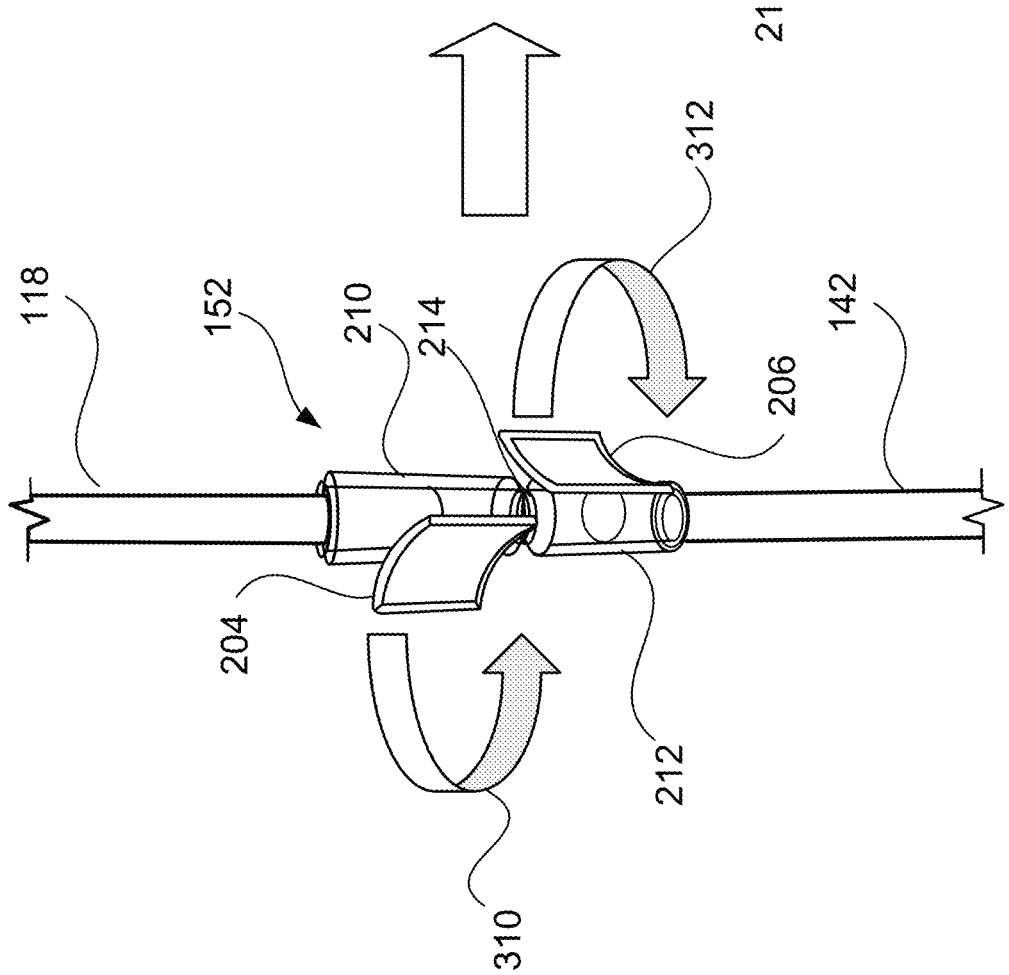
FIG. 6

MEDICAL FLUID LINE CONNECTION DEVICES

TECHNICAL FIELD

This disclosure relates to medical line fluid connection devices.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a medical fluid line connector includes a body defining a central opening extending therethrough, a first projection extending from a first portion of the body, and a second projection extending from a second portion of the body, the second projection being circumferentially and axially offset from the first projection. The first portion of the body and second portion of the body are configured to separate from one another in response to a threshold amount of force being applied to the first projection and the second projection to rotate the first portion of the body and second portion of the body relative to one another.

Implementations can include one or more of the following features in any combination.

In some implementations, applying the threshold amount of force to the first projection and the second projection comprises simultaneously applying a counterclockwise rotational force to the first projection and a clockwise rotational force to the second projection.

In certain implementations, the first portion of the body and the second portion of the body are connected by a frangible portion, and application of the threshold amount of force to the first projection and the second projection causes the frangible portion to break.

In some implementations, a thickness of the frangible portion is smaller than a thickness of the first portion of the body or a thickness of the second portion of the body.

In certain implementations, the first projection includes a first curved wing.

In some implementations, the second projection includes a second curved wing.

In certain implementations, the first curved wing and the second curved wing are each sized to accommodate an adult thumb.

In some implementations, the first curved wing and the second curved wing are each configured to receive a force sufficient to separate the first and second portions of the body from one another without separating the first curved wing or the second curved wing from the body.

In certain implementations, the first projection includes a first linear rib.

In some implementations, the second projection includes a second linear rib.

In certain implementations, the first projection includes a first flat, rectangular projection.

In some implementations, the second projection includes a second flat, rectangular projection.

In certain implementations, the first projection is circumferentially spaced apart from the second projection by 105 degrees to 115 degrees.

In some implementations, the first projection is integrally molded with the first portion of the body, and the second projection is integrally molded with the second portion of the body.

In certain implementations, the first and second projections are discrete components that are coupled to the first and second portions, respectively, of the body.

In another aspect, a method of disconnecting a fluid bag from a fluid line includes applying a counterclockwise rotational force to a first projection extending from a first portion of a body of a connector coupled to the fluid line and an inlet of the fluid bag, and simultaneously applying a clockwise rotational force to a second projection extending from a second portion of the body of the connector, the second portion of the body being axially offset from the first portion of the body. Simultaneously applying the counterclockwise rotational force to the first projection and the clockwise rotational force to the second projection generates a twisting force sufficient to separate the first portion of the body from the second portion of the body.

Implementations can include one or more of the following features in any combination.

In some implementations, simultaneously applying the counterclockwise rotational force to the first projection and the clockwise rotational force to the second projection causes a frangible portion of the body of the connector to break.

In certain implementations, the method includes closing a clamp positioned along the fluid line or along the inlet of the fluid bag.

In some implementations, the counterclockwise rotational force is in a range of 60 oz-in to 120 oz-in and the clockwise rotational force is in a range of 60 oz-in to 120 oz-in.

In certain implementations, the twisting force is a force that exceeds 60 oz-in.

In some implementations, the first projection is a first curved wing and the second projection is a second curved wing.

In certain implementations, applying the counterclockwise rotational force to the first projection includes using a first thumb to push against the first projection in a first direction, and applying the clockwise rotational force to the second projection includes using a second thumb to push against the second projection in a second direction opposite the first direction.

In a further aspect, a system includes a medical treatment device, a fluid bag, a fluid line configured to be secured to the medical treatment device and fluidly coupled to the fluid bag, and a connector configured to fluidly couple the fluid bag to the fluid line. The connector includes a body defining a central opening extending therethrough, a first projection extending from a first portion of the body, and a second projection extending from a second portion of the body, the second projection being axially and circumferentially offset from the first projection. The first portion of the body and the second portion of the body are configured to separate from one another in response to a threshold amount of force being applied to the first projection and the second projection to generate a twisting force that rotates the first portion of the body and second portion of the body relative to one another.

Implementations can include one or more of the following features in any combination.

In some implementations, the medical treatment device is a dialysis machine.

In certain implementations, the fluid bag is configured to collect spent dialysate during a dialysis treatment.

In some implementations, the system includes a second fluid bag, and a second connector configured to fluidly couple the second fluid bag to the fluid line.

In certain implementations, the first projection includes a first curved wing; and the second projection includes a second curved wing.

Implementations can include one or more of the following advantages.

In some implementations, a breakable connector that fluidly connects a fluid line to a fluid bag can enable a user to easily disconnect the fluid bag from the fluid line in order to transport and/or dispose of the fluid contained within the bag.

In some implementations, the breakable connector can be broken through the application of a twisting force on the breakable connector, which allows for intuitive and easy disconnection of the fluid bag from the fluid line.

In certain implementations, the breakable connector can be broken by applying a twisting force to projections that extend from the body of the breakable connector, rather than by applying the force directly to the body of the breakable connector. In such implementations, the amount of torque applied to the connector is increased, making it easier for a user to break the connector and disconnect a fluid bag from a fluid line.

The breakable connector can also include projections configured to conform to the user's thumbs when the user is holding the connector, thereby improving the user's grip on the connector and making the breakable connector more ergonomic and user-friendly.

The details of one or more embodiments are set forth in the accompanying drawings and the description below. Other aspects, features, and advantages of the disclosure will be apparent from the description and drawings, and from the claims.

DESCRIPTION OF DRAWINGS

FIGS. 6 and 7 are schematic illustrations of a process of separating a fluid line from a fluid bag by breaking the breakable connector of FIG. 2.

DETAILED DESCRIPTION

Figure 1:
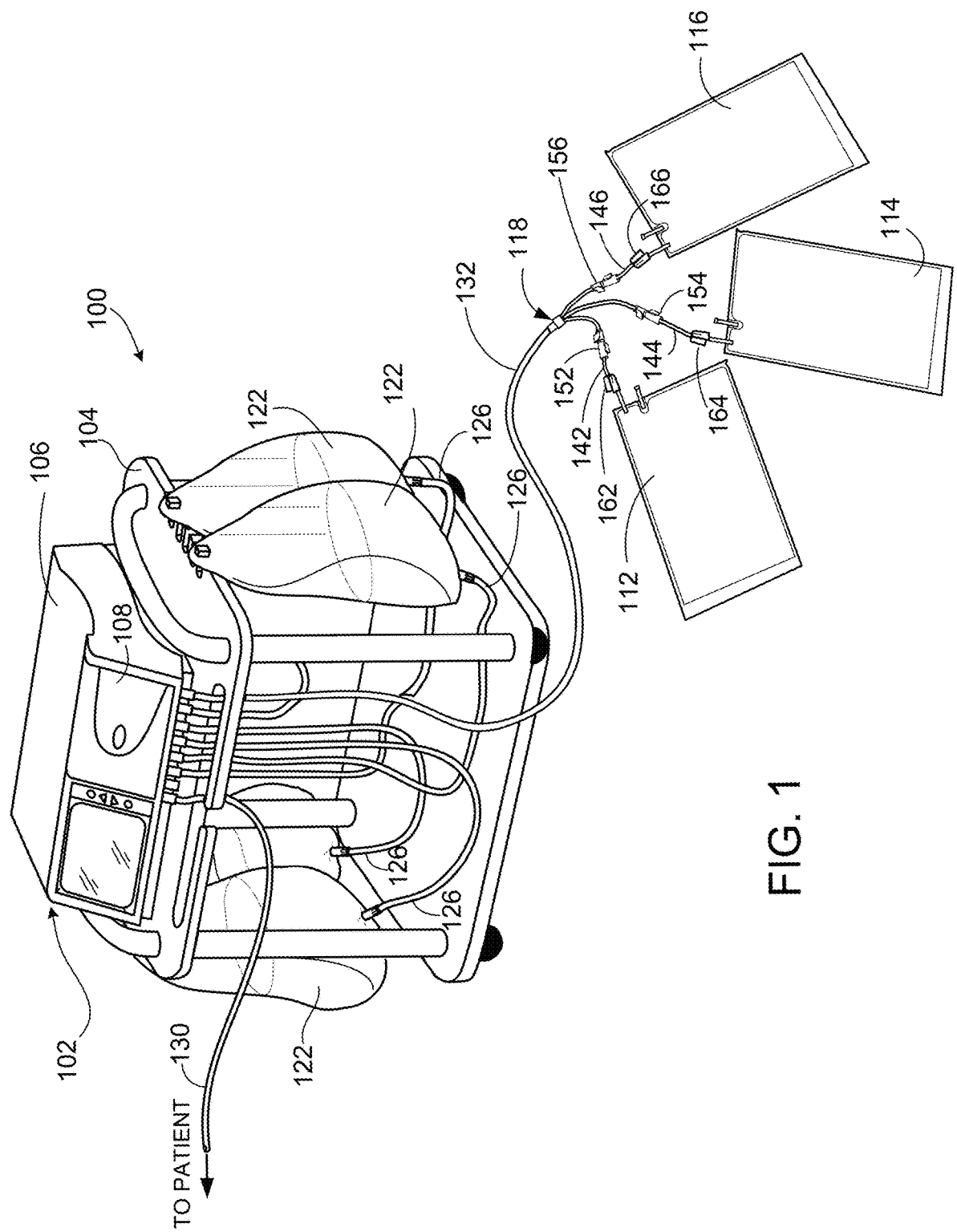
FIG. 1 is a perspective view of a peritoneal dialysis ("PD") system that includes a PD machine and a disposable set including, among other components, fluid drain bags that are fluidly coupled to associated fluid lines using breakable connectors.

FIG. 1 depicts an example peritoneal dialysis ("PD") system 100 that can be used to perform PD treatments. A PD treatment typically begins by draining fluid from a patient's peritoneal cavity. Once the patient's peritoneal has been drained, the patient's peritoneal cavity is filled with dialysate, which then dwells in the patient's peritoneal cavity for a period of time. After delivering the dialysate to the patient's peritoneal cavity and permitting the dialysate to dwell in the peritoneal cavity for a predetermined period of time, the dialysate is drained from the peritoneal cavity. The process of draining, filling, dwelling, and draining is repeated throughout a PD treatment cycle. Fluid drained from the patient's peritoneal cavity during the draining phase of treatment can be collected in one or more drain bags 112, 114, 116.

Still referring to FIG. 1, the PD system 100 includes a PD cycler 102 and a disposable set connected thereto that can together be used to perform automated peritoneal dialysis (APD) treatments. The PD cycler 102 is designed to automatically infuse, dwell, and drain dialysate to and from the patient's peritoneal cavity. An APD treatment typically lasts for several hours, often beginning with an initial drain cycle to empty the peritoneal cavity of used or spent dialysate.

The PD cycler 102, as shown in FIG. 1, is seated on a cart 104. The PD cycler 102 includes a housing 106, a door 108, and a cassette interface that contacts a disposable PD cassette of the disposable set when the cassette is disposed within a cassette compartment formed between the cassette interface and the closed door 108.

The disposable set further includes dialysate bags 122 that are suspended from fingers on the sides of the cart 104. The dialysate bags 122 are connected to the cassette via dialysate bag lines 126. The dialysate bag lines 126 can be used to pass dialysate from dialysate bags 122 to the cassette during a fill phase of an APD treatment cycle.

A patient line 130 and a drain line 132 are connected to the cassette. The patient line 130 can be connected to a patient's abdomen via a catheter and can be used to pass dialysate back and forth between the cassette and the patient's peritoneal cavity during treatment. The drain line 132 can be fluidly connected to a set of drain bags 112, 114, 116 and can be used to pass spent dialysate from the cassette to the drain bags 112, 114, 116 during treatment.

As depicted in FIG. 1, each of the drain bags includes an inlet line 142, 144, 146 extending therefrom that fluidly connects the respective drain bag 112, 114, 116 to the drain line 132 of the PD system 100. During the drain phase of APD treatment, fluid is pumped by the PD cycler 102 from the PD cassette into the drain line 132, and into the drain bags 112, 114, 116 through the inlet lines 142, 144, 146 of the drain bags 112, 114, 116. Each of the inlet lines 142, 144, 146 is coupled to the drain line 132 using a split connector 118 that causes fluid flowing through the drain line 132, such as spent dialysate, 132 to be divided along inlet lines 142, 144, 146. For example, the connector 118 allows fluid in the drain line 132 to flow into each of the drain bags 112, 114, 116 via gravity. As a result, if one of the drain bags 112 becomes more full compared to the other drain bags 114, 116 (e.g., as a result of how the drain bag 112 is positioned on the floor), a negative pressure will be against the fluid flowing through the inlet line 142 of the drain bag 112, which will cause fluid flowing through the connector 118 to be diverted to the other drain bags 1114, 116 until all three drain bags 112, 114, 116 contain a similar amount of fluid.

Each of the inlet lines 142, 144, 146 include a breakable connector 152, 154, 156 positioned along the respective inlet line 142, 144, 146. The breakable connectors 152, 154, 156 fluidly couple the drain line 132 to the drain bags 112, 114, 116 such that during treatment, the breakable connectors 152, 154, 156 allow fluid to pass from the drain line 132, the connector 118, and the respective inlet lines 142, 144, 146, and into the respective drain bags 112, 114, 116.

The breakable connectors 152, 154, 156 can be used to fluidly disconnect each of the drain bags 112, 114, 116 from the drain line 132, which enables a user to more easily dispose of the fluid contained within the drain bags 112, 114, 116. For example, at the end of treatment or whenever one or more of the drain bags 112, 114, 116 is filled with spent dialysate, the filled drain bag(s) 112, 114, 116 can be fluidly disconnected from the drain line 132 by breaking the respective breakable connector 152, 154, 156 coupled to the inlet 142, 144, 146 of the respective drain bag 112, 114, 116. By including a breakable connector 152, 154, 156 along the inlet 142, 144, 146 of each drain bag 112, 114, 116, the drain bags 112, 114, 116 can be individually disconnected from the drain line 132, making it easier to transport and empty the fluid-filled drain bags 112, 114, 116.

Clamps 162, 164, 166 are also positioned along the inlet lines 142, 144, 146 of each drain bag 112, 114, 116. The clamps 162, 164, 166 can be used to control flow of fluid into and out of the drain bags 112, 114, 116. For example, during the PD treatment, one or more of the clamps 162, 164, 166 can be opened to allow fluid to flow from the drain line 132 into the associated drain bag(s) 112, 114, 116. In some implementations, all of the clamps 162, 164, 166 are open during the drain phase of PD treatment. At the end of PD treatment, or whenever a drain bag 112, 114, 116 has become filled with fluid, the respective clamp 162, 164, 166 can be closed to prevent additional fluid from flowing into the drain bag 112, 114, 116 and prevent fluid from flowing out of the drain bag 112, 114, 116 when the drain bag 112, 114, 116 is disconnected from the drain line 132 using the respective breakable connector 152, 154, 156.

Figure 2:
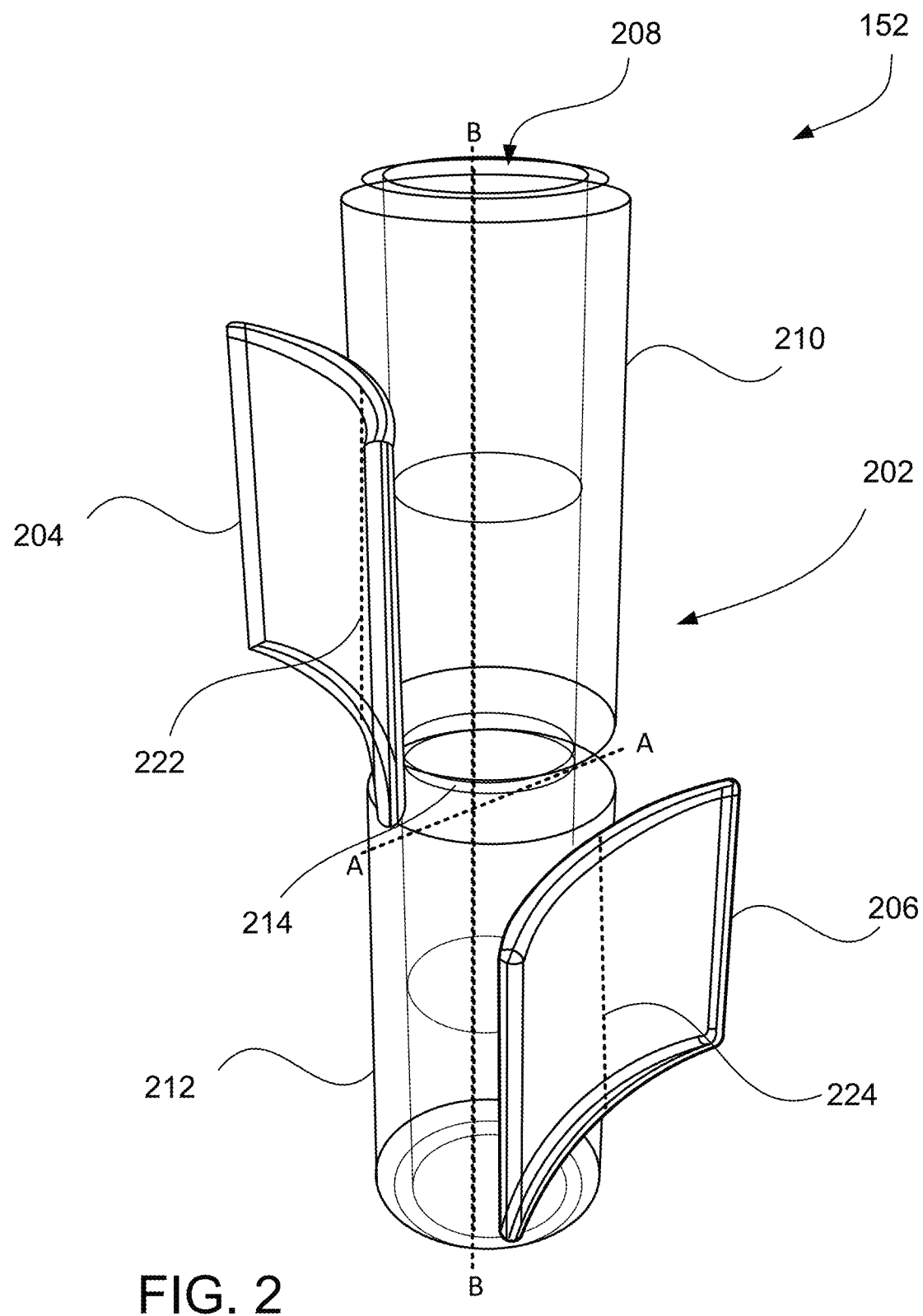
FIG. 2 is a perspective view of one of the breakable connectors of the PD system of FIG. 1.

FIG. 2 depicts the breakable connector 152 that is used to fluidly couple the drain bag 112 to the drain line 132 in the PD system 100 illustrated in FIG. 1. It should be understood that the breakable connectors 154 and 156 are identical to the breakable connector 152. Therefore, the breakable connectors 154 and 156 will not be separately described in detail.

As can be seen in FIG. 2, the breakable connector 152 includes a body 202 with two projections 204, 206 that extend from the body 202. The projections 204, 206 are sized, shaped, and arranged to receive thumbs of a user when the connector 152 is to be broken during use.

Figure 3:
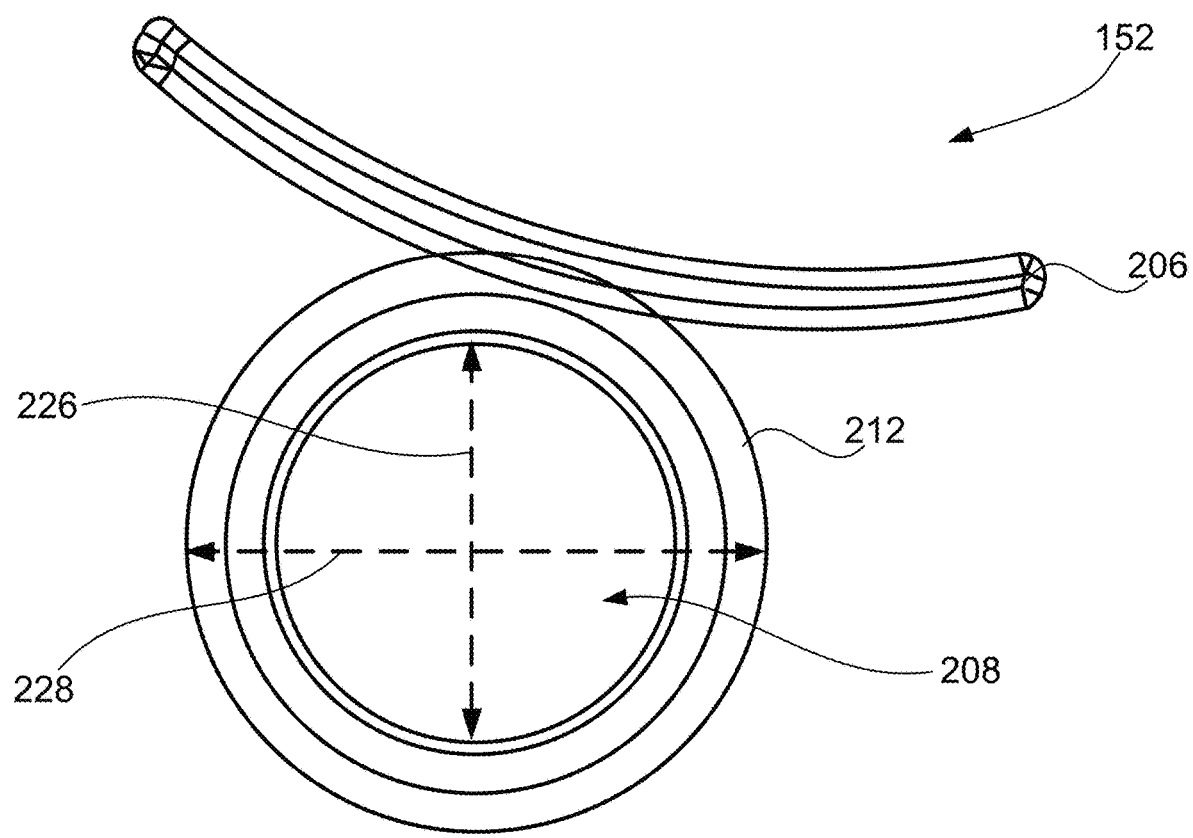
FIGS. 3 and 4 are cross section schematic illustrations taken along lines A-A and B-B, respectively, in FIG. 2.

FIG. 3 depicts a cross-sectional view of the breakable connector 152 along the A-A axis depicted in FIG. 2. As can be seen in FIGS. 2 and 3, body 202 of the breakable connector 152 is generally tubular shaped and defines a central opening 208 therethrough that extends along the length of the body 202. The central opening 208 allows for fluid to flow freely through the breakable connector 152. For example, when the breakable connector is coupled at a first end to a fluid line (e.g., connector 118 or drain line 132 of FIG. 1) and coupled at a second end to a drain bag inlet (e.g., inlets 142, 144, 146 of FIG. 1), any fluid flowing through the fluid line will flow through the central opening 208 in the breakable connector 152 and into the drain bag. In some implementations, the diameter 226 of the central opening 208 ranges from about 0.66 centimeters to about 0.82 centimeters.

Referring back to FIG. 2, the body 202 of the breakable connector 152 includes a first portion 210 and a second portion 212 that are offset from one another along the length of the body 202 of the breakable connector 152. As will be described in further detail herein, the first portion 210 of the body 202 and the second portion 212 of the body 202 are connected to one another by a frangible portion 214 of the body 202. As depicted in FIG. 2, the body 202 of the breakable connector 152 is formed of a transparent material or a semi-transparent material.

A first projection 204 extends from the first portion of the body 202 and a second projection 206 extends from the second portion 212 of the body 202. The first and second projections 204, 206 of the breakable connector 152 are integrally molded to the first and second portions 210, 212 of the body 202, respectively. For example, in some implementations, the breakable connector 152 is formed using injection molding techniques that integrally mold the body 202 and projections 204, 206 of the breakable connector 152.

The overall length of the body 202 can range from about 1.90 centimeters to about 2.90 centimeters, and the length the first portion 210 and the length of the second portion 212 can each range from about 0.95 centimeters to about 1.45 centimeters. In addition, as depicted in FIG. 3, the outer diameter 228 of the second portion 212 of the body 202 can range from about 0.8 centimeters to about 1 centimeters. Similarly, the outer diameter of the first portion 210 of the body 202 can range from about 0.8 centimeters to about 1 centimeter. As depicted in FIG. 2, the outer diameters of the first and second portions 210, 212 of the body 202 are equal. In some implementations, the outer diameter of the first portion 210 of the body 202 and the outer diameter 228 of the second portion 212 of the body 202 are about 0.99 centimeters.

Figure 4:
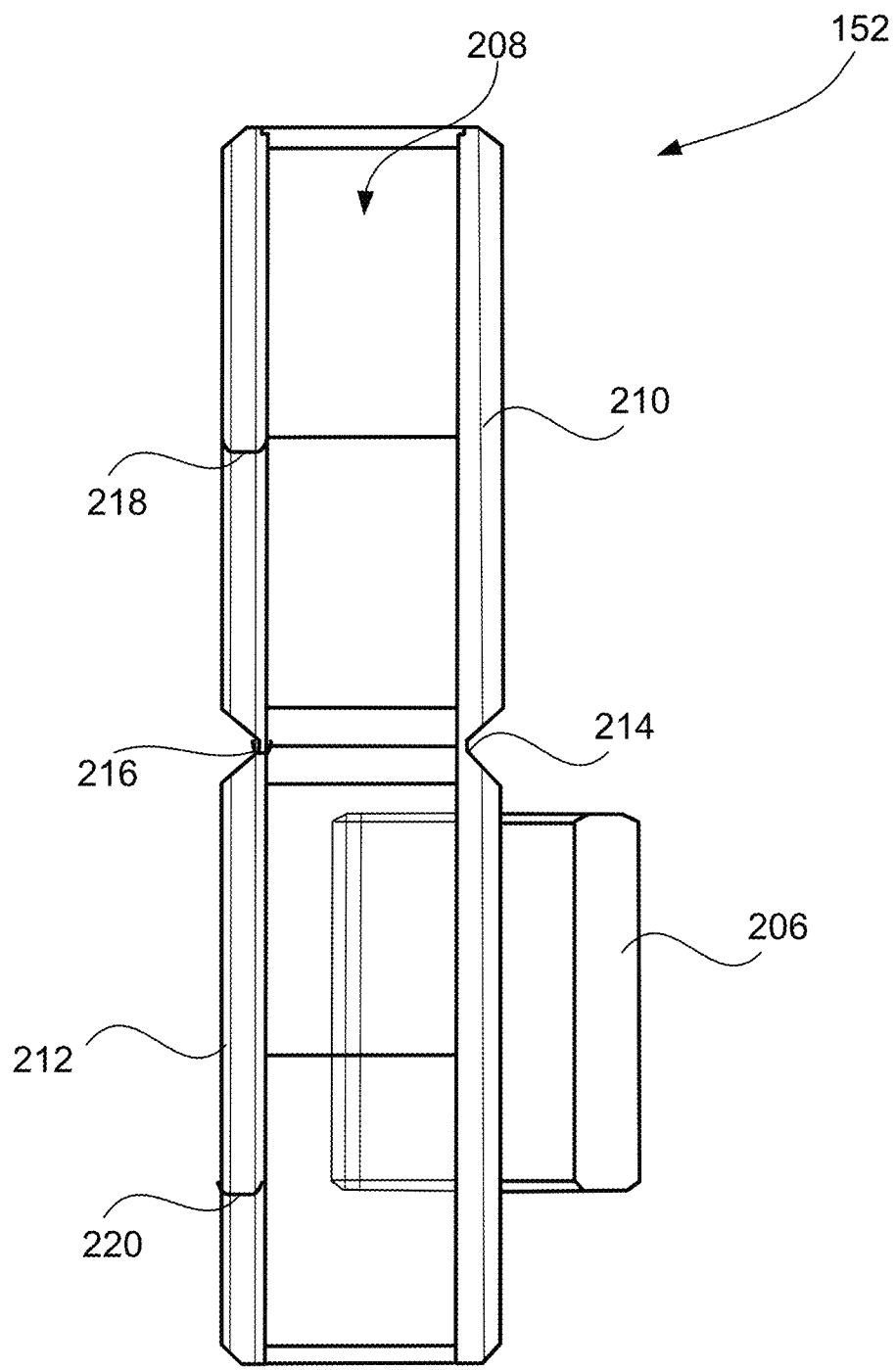

FIG. 4 depicts a cross-sectional view of the breakable connector 152 along the B-B axis depicted in FIG. 2. As can be seen in FIGS. 2 and 4, the first portion 210 of the body 202 and the second portion 212 of the body 202 are each tapered and connected to one another by a frangible portion 214 of the body 202. The thickness 216 of the wall of the frangible portion 214 of the body is less than the thickness 218 of the wall of the first portion 210 of the body 202 and the thickness 220 of the wall of the second portion 212 of the body 202. As a result of the decreased wall thickness along the frangible portion 214, opposing forces placed on the first and second portions 210, 212 of the body 202 cause the frangible portion 214 of the body 202 to fail and break, which causes the first and second portions 210, 212 of the body 202 to separate from one another. For example, as will be described in detail herein, opposing forces (e.g., torque) can be simultaneously applied to the first projection 204 and the second projection 206 to generate a twisting force that rotates the first portion 210 of the body 202 and second portion 212 of the body 202 relative to one another, causing the frangible portion 214 of the body 202 to shear or otherwise fail and separate the first and second portions 210, 212 of the body 202.

In some implementations, the thickness 218, 220 of the wall of the body 202 along each of the first and second portions 210, 212 of the body is about 0.25 centimeters to about 0.30 centimeters. In some implementations, the thickness 216 of wall of the frangible portion 214 of the body is about 0.015 centimeters to about 0.025 centimeters.

The frangible portion 214 can be configured to fail (e.g., break or shear) when a threshold amount of twisting force (torque) is applied to the first and second portions 210, 212 of the body 202. In some implementations, the threshold amount of twisting force that causes the frangible portion 214 to fail and separate the first and second portions 210, 212 of the body 202 can range from 60 oz-in to 120 oz-in (0.42 N-m to 0.84 N-m).

As can be seen in FIG. 2, the first projection 204 is shaped as a curved wing that extends outward in opposing directions from a centerline 222 of the first projection 204 and away from the body 202 of the breakable connector 152. The second projection 206 is also shaped as a curved wing and extends outward in opposing directions from a centerline 224 of the second projection 206 and away from the body 202 of the breakable connector 152.

Figure 7:
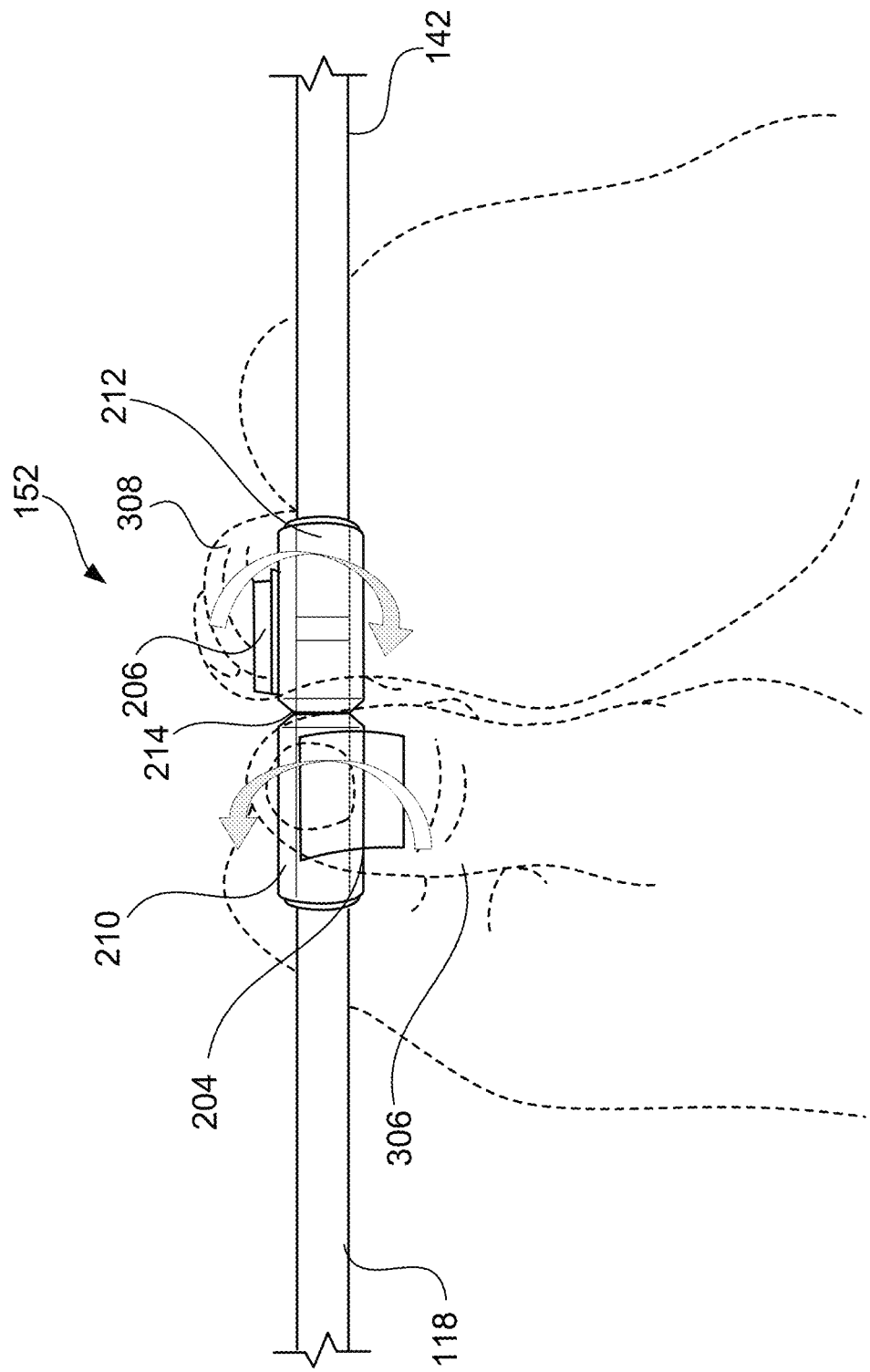

As can be seen in FIG. 7, each of the projections 204, 206 is sized and shaped to accommodate and conform to a respective thumb 306, 308 of an adult user. In addition, each projection 204, 206 is sized to prevent the projections 204, 206 from breaking apart from the body 202 when a rotational force sufficient to separate the first and second portions 210, 212 of the body 202 is applied to the projections 204, 206. For example, the surface area of each of the projections 204, 206 can range from about 1.60 square centimeters to 3.2 square centimeters. The length of each projection 204, 206 can range from 1.40 centimeters to 1.88 centimeters and the width of each projection 204, 206 range from 1.25 centimeters to 2 centimeters. In some implementations, the length of each projection 204, 206 is about 1.35 centimeters and the width of each projection 204, 206 is about 1.60 centimeters.

As can be seen in FIG. 2, the first projection 204 and the second projection 206 are axially offset from one another along the length of the body 202. The first projection 204 and the second projection 206 can be axially offset from one another in a range of 0.75 centimeters to 0.82 centimeters along the length of the body 202.

Figure 5:
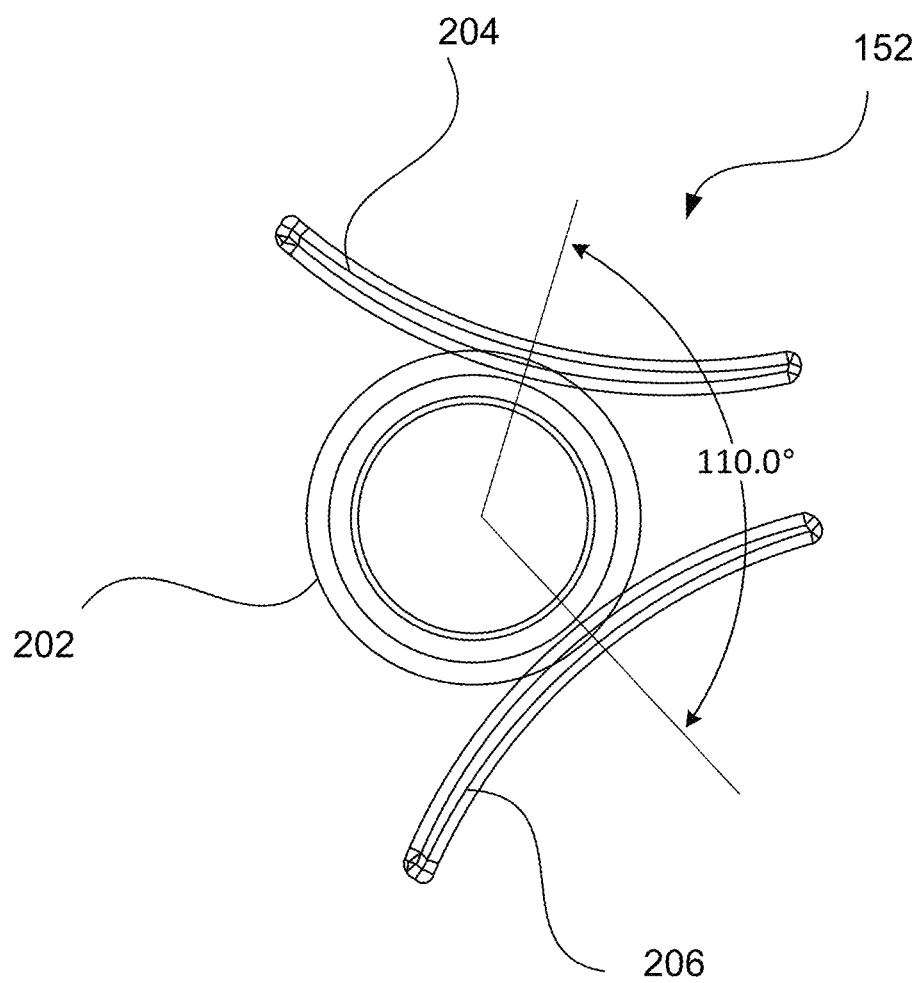
FIG. 5 is a top view of the breakable connector of FIG. 2.

As can be seen in FIGS. 2 and 5, the first projection 204 and the second projection 206 are also circumferentially offset from one another about the B-B axis of the body 202. For example, the centerline 222 of the first projection 204 and the centerline 224 of the second projection 206 are circumferentially offset from one another in a range of 105 degrees to 115 degrees. In some implementations, the centerline 222 of the first projection 204 is 110 degrees apart from the centerline 224 of the second projection 206.

The relative positioning of the first projection 204 and the second projection 206 on the body 202 of the breakable connector 152 enables a user to easily grip the breakable connector 152 and results in increased the twisting force (torque) when the user applies opposing rotational forces to the first and second projections 204, 206. As a result, the breakable connector 152 allows a user to easily separate a drain bag (e.g., drain bags 112, 114, 116 of FIG. 1) from a drain line (e.g., drain line 132 of FIG. 1) of a blood treatment machine (e.g., PD cycler 102 of FIG. 1), which can be particular beneficial for users with reduced hand strength or dexterity, such as users with arthritis or certain elderly users. In addition, by enabling the user to individually separate each of the drain bags 112, 114, 116 from the PD cycler 102 using the breakable connectors 152, 154, 156, the user is able to more easily lift and transport the drain bags 112, 114, 116 for disposal of the fluid contained in the drain bags 112, 114, 116. This is particularly beneficial for users with muscle weakness for whom carrying multiple filled drain bags simultaneously would be difficult, such as some elderly users.

FIGS. 6 and 7 depict a process of disconnecting the drain bag 112 from the drain line 132 using the breakable connector 152 of FIG. 2. As depicted in FIGS. 2 and 6, the inlet 142 of the drain bag 112 is fluidly coupled to the drain line 132 via the breakable connector 152. In particular, the first portion 210 of the body 202 of the breakable connector 152 is connected to a portion of the split connector 118 and the second portion 212 of the body 202 of the connector 152 is connected to the inlet 142 of the drain bag, and, prior to disconnection of the inlet 142, fluid can flow from the drain line 132, through the split connector 118, through the breakable connector 152, and into the inlet 142 of the drain bag 112.

As described above, the first portion 210 of the body 202 and the second portion 212 of the body 202 can be separated from one another by applying a twisting force to the body 202 of the breakable connector 152. For example, as depicted in FIG. 6, a twisting force can be applied to the body 202 of the breakable connector 152 by applying a counterclockwise rotational force 310 to the first portion 210 of the body 202 while simultaneously applying a clockwise rotational force 312 to the second portion 212 of the body 202. Simultaneously applying counterclockwise and clockwise rotational forces 310, 312 to the first and second portions 210, 212 of the body 202, respectively, can generate a twisting force (torque) that exceeds the strength of the frangible portion 214 of the body 202, causing the first and second portions 210, 212 of the body 202 to rotate relative to one another and causing the frangible portion 214 of the body 202 to break. The threshold amount of twisting force required to break the frangible portion 214 of the body 202 and separate the first and second portions 210, 212 of the body 202 can range from about 60 oz-in to about 120 oz-in (about 0.42 N-m to about 0.84 N-m).

FIG. 7 depicts a user applying twisting force to the body 202 of the breakable connector 152 using the first and second projections 204, 206 extending from the body 202 of the breakable connector 152. As depicted in FIG. 7, the user can place his or her left thumb 306 on the first projection 204 and can place his or her right thumb 308 on the second projection 206. The user can then use his or her thumbs 306, 306 to press on the projections 204, 206 and simultaneously apply a counterclockwise rotational force to the first projection 204 and apply a clockwise rotational force to the second projection 206. The opposing rotational forces applied to the first and second projections 204, 206 are transferred to the first portion 210 of the body 202 and the second portion 212 of the body 202, respectively, generating torque across the frangible portion 214 of the body 202 and causing the first portion 210 and the second portion 212 of the body 202 to rotate relative to and separate from one another. The curved shape of the projections 204, 206 conforms to the shape of the user's thumbs 306, 308 to improve the user's grip on the breakable connector 152 and assists the user in applying a rotational force to each of the projections 204, 206. In some implementations, the separation of the first and second portions 210, 212 of the body 202 from one another involves applying a counterclockwise force to the first projection 204 and applying a clockwise force to the second projection 206.

As previously discussed and as depicted in FIGS. 2 and 6, separation of the first portion 210 and second portion 212 of the body 202 fluidly disconnects the drain bag 112 from the blood treatment system by separating the inlet 142 of the drain bag 112 from the split connector 118, which fluidly disconnects the inlet 142 from the drain line 132. The clamp 162 positioned along the inlet 142 of the drain bag 112 can be closed prior to applying the twisting force to the breakable connector 152 in order to prevent fluid from leaking out of the drain bag 112 after fluidly disconnecting the inlet 142 of the drain bag 112 from the drain line 132.

It should be understood that the breakable connector 154, clamp 164, and inlet 144 can be operated in the same manner as the breakable connector 152, clamp 162, and inlet 142 in order to fluidly disconnect the drain bag 114 from the drain line 132 and dispose of the contents of the drain bag 114. Similarly, the breakable connector 156, clamp 166, and inlet 146 can be operated in the same manner as the breakable connector 152, clamp 162, and inlet 142 in order to fluidly disconnect the drain bag 116 from the drain line 132 and dispose of the contents of the drain bag 116. Therefore, the process of disconnecting the drain bags 114 and 116 from the drain line 132 will not be separately described in detail.

While certain embodiments have been described above, other embodiments are possible.

For example, while the PD system 100 has been depicted as including three drain bags 112, 114, 116 connected to the drain line 132 using three respective breakable connectors 152, 154, 156, other numbers of drain bags can be connected to the drain line 132. For example, in some implementations, a single drain bag is coupled to the drain line 132 using a single breakable connector. Alternatively, two drain bags can be coupled to the drain line 132 using two separate breakable connectors. In some implementations, four or more drain bags are coupled to the drain line 132 using a respective number of breakable connectors.

While the first portion 210 and second portion 212 of the body 202 of the breakable connector 152 have been described as being separated from one another by applying a twisting force to the breakable connector 152, in some implementations, the first and second portions 210, 212 of the body 202 of the breakable connector 152 are separated from one another by applying a bending force to the breakable connector 152. For example, a user can use the projections 204, 206 to grip the breakable connector 152 with his or her fingers and apply a bending force to the body 202 of the breakable connector 152 until the frangible portion 214 of the body 202 breaks and the first portion 210 of the body 202 separates from the second portion 212 of the body 202.

While the body 202 of the breakable connector 152 has been described as being formed of a material that is transparent or semi-transparent, in some implementations, the body 202 of the breakable connector 152 is formed of an opaque material.

While the projections 204, 206 have been described as being integrally molded with the body 202 of the breakable connector 152, in some implementations, the body 202 of the breakable connector 152 is molded separately from the projections 204, 206 and the projections 204, 206 are attached to body 202 (e.g., using an adhesive, a weld, a snap-fit attachment, or other mechanical attachment).

While the clamps 162, 164, 166 for controlling flow into and out of the drain bags 112, 114, 116 have been described as being positioned along the inlet lines 142, 144, 146 of the drain bags 112, 114, 116, in some implementations, an additional clamp is positioned along the drain line 132 to control the flow of fluid from the drain line 132.

While the twisting force applied to the breakable connector 152 has been described as being generated by applying a counterclockwise rotational force 310 to the first projection 204 while simultaneously applying a clockwise rotational force 312 to the second projection 206, in some implementations, the twisting force is generated by applying a clockwise rotational force to the first projection 204 while simultaneously applying a counterclockwise rotational force to the second projection 206.

Figure 8:
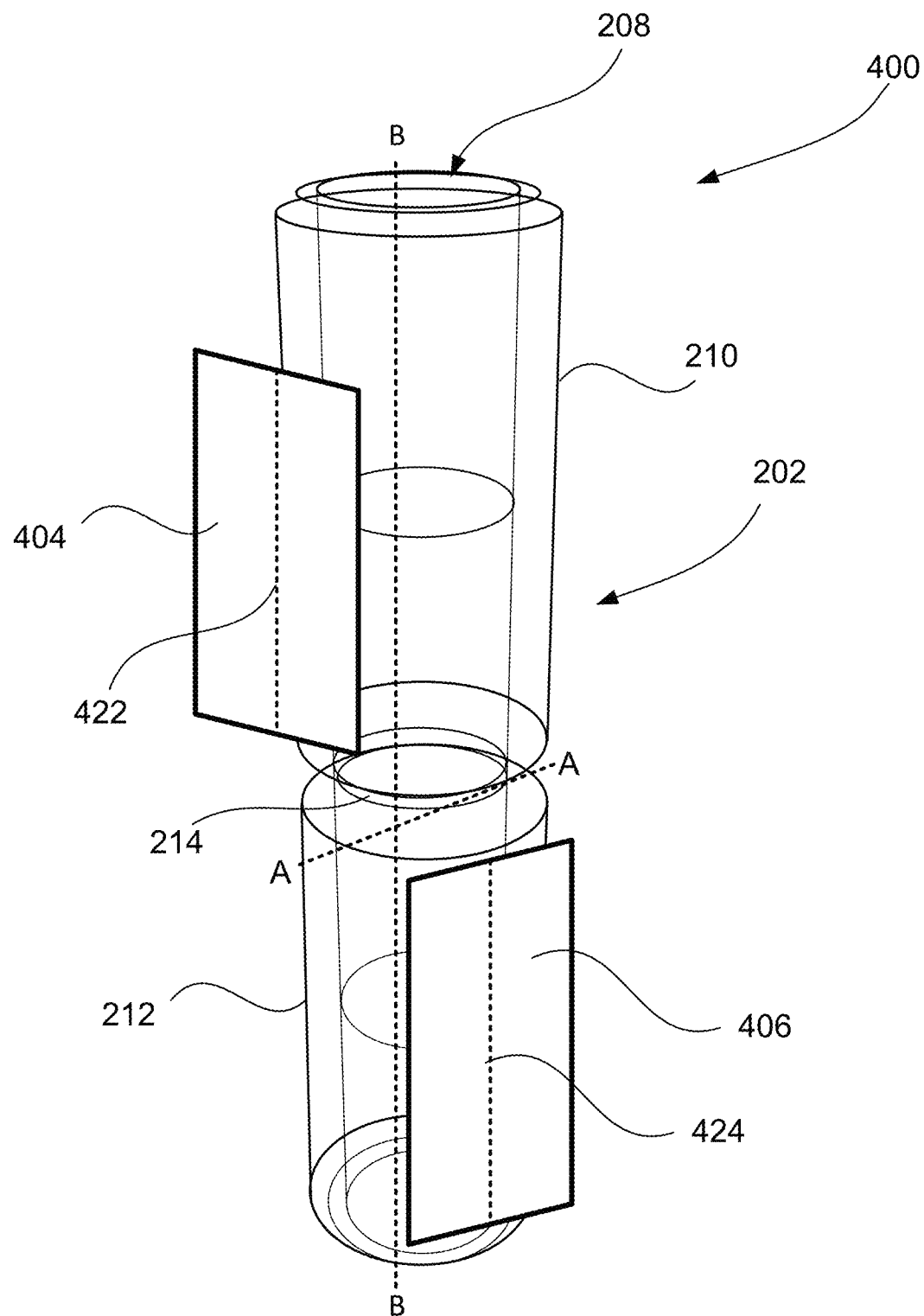
FIG. 8 is a perspective view of an alternative breakable connector that can be used for connecting the fluid bags of FIG. 1 to their associate fluid lines.

While the projections 204, 206 of the breakable connector 152 have been described as having a curved shape, other projection shapes can be used to enable a user to apply a twisting force to the body of the breakable connector. For example, as depicted in FIG. 8, a breakable connector 400 includes a pair of flat, rectangular-shaped projections 404, 406, rather than curved, wing-shaped projections (such as projections 204, 206 of FIG. 2). The first flat, rectangular-shaped projection 404 extends from the first portion 210 of the body 202 and the second flat, rectangular-shaped projection 406 extends from a second portion 212 of the body 202.

In some implementations, the breakable connector 400 is formed using injection molding techniques to integrally mold the body 202 and projections 404, 406. In some implementations, the body 202 of the breakable connector 400 is molded separately from the projections 404, 406 and the projections 404, 406 are attached to body 202 (e.g., using an adhesive).

Each of the flat, rectangular-shaped projections 404, 406 is sized to accommodate the thumb of an adult user and to prevent the projections 404, 406 from breaking apart from the body 202 of the breakable connector 400 when forces sufficient to separate the first and second portions 210, 212 of the body 202 from one another are applied to the projections 404, 406. For example, the surface area of each of the projections 404, 406 can range from about 1.6 square centimeters to 3.2 square centimeters. The length of each projection 404, 406 can range from 1.4 centimeters to 1.88 centimeters and the width of each projection 404, 406 range from 1.25 centimeters to 2 centimeters.

As can be seen in FIG. 8, the first projection 404 and the second projection 406 are axially offset from one another along the length of the body 202. For example, the first projection 404 and the second projection 406 can be axially offset from one another in a range of 0.75 centimeters to 0.82 centimeters along the length of the body 202. The first projection 404 and the second projection 406 are also circumferentially offset from one another about the B-B axis of the body 202. For example, the centerline 422 of the first projection 404 and the centerline 424 of the second projection 406 are circumferentially offset in a range of 105 degrees apart to 115 degrees apart.

Similar to projections 204, 206 of the breakable connector 152 in FIGS. 2-7, opposing rotational forces can be applied to the projections 404, 406 of the breakable connector 400 in order to generate a twisting force that rotates the first portion 210 and the second portion 212 of the body 202 of the breakable connector 400 relative to one another and separates the first and second portions 210, 212 of the body 202 from one another. For example, a user can use his or her thumbs to press against each of the projections 404, 406 to apply opposing rotational forces to the projections 404, 406, which rotates the first and second portions 210, 212 of the body 202 relative to one another and breaks a frangible portion 214 of the body 202, separating the first and second portions 210, 212 of the body 202 from one another. In some implementations, the frangible portion 214 breaks and the first and second portions 210, 212 of the body 202 of the breakable connector 400 are separated from one another when a counterclockwise rotational force in a range of 60 oz-in to 120 oz-in (0.42 N-m to 0.84 N-m) is applied to the first projection 404 and a clockwise force in a range of 60 oz-in to 120 oz-in (0.42 N-m to 0.84 N-m) is applied to the second projection 406. In some implementations, the frangible portion 214 breaks and the first and second portions 210, 212 of the body are separated from one another by applying a clockwise rotational force to the first projection 404 and applying a counterclockwise rotational force to the second projection 406.

In some implementations, a user can use the projections 404, 406 to grip the breakable connector 400 and apply a bending force to the body 202 of the breakable connector 400 until the frangible portion 214 of the body 202 breaks and the first portion 210 of the body 202 separates from the second portion 212 of the body 202.

Figure 9:
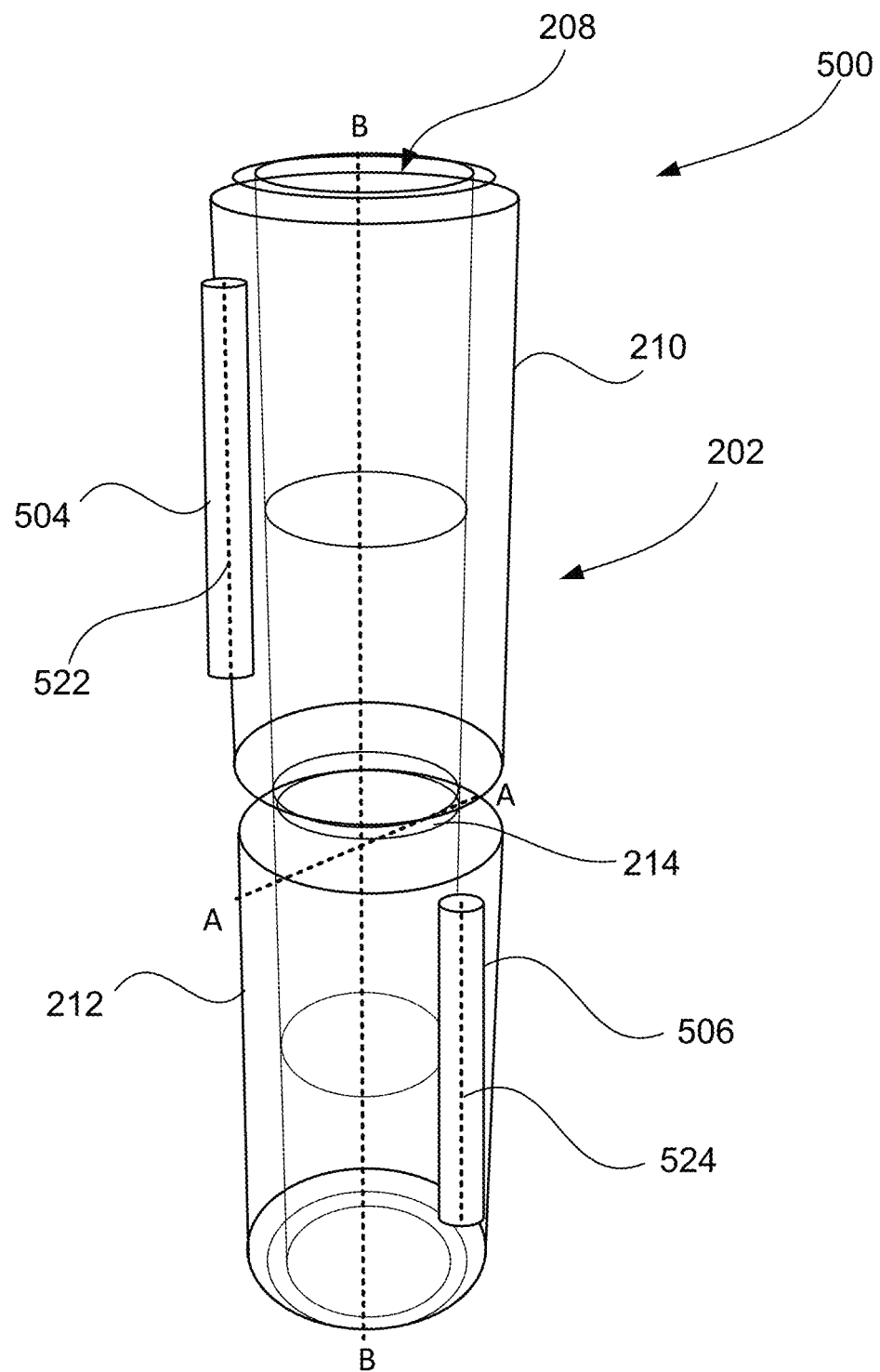
FIG. 9 is a perspective view of another type of breakable connector that can be used for connecting the fluid bags of FIG. 1 to their associated fluid lines.

As depicted in FIG. 9, another breakable connector 500 includes a pair of linear rib projections 504, 506, rather than curved, wing-shaped projections (such as projections 204, 206 in FIG. 2). The first projection 504 extends along the first portion 210 of the body 202 and the second projection 506 extends along a second portion 212 of the body 202. The first and second portions 210, 212 of the body 202 are axially offset from one another and connected to one another by a frangible portion 214 of the body 202. Similar to projections 204, 206 in FIG. 2, the linear rib projections 504, 506 can be used to apply a twisting force to the breakable connector 500 in order to separate a first portion 210 of the body 202 of the breakable connector 500 from a second portion 212 of the body 202 of the breakable connector 500.

In some implementations, the breakable connector 500 is formed using injection molding techniques to integrally mold the body 202 of the breakable connector 500 and the projections 504, 506 extending from the body 202 of the breakable connector 500. In some implementations, the body 202 of the breakable connector 500 is molded separately from the projections 504, 506, and the projections 504, 506 are then attached to body 202 (e.g., using an adhesive).

Each projection 504, 506 of the breakable connector 500 is sized to prevent the projections 504, 506 from breaking apart from the body 202 when a twisting force sufficient to separate the first and second portions 210, 212 of the body 202 from one another is applied to the projections 504, 506. For example, the surface area of each of the projections 504, 506 can range from about 0.40 square centimeters to about 0.50 square centimeters. The length of each projection 504, 506 can range from about 1.90 centimeters to about 2.90 centimeters and the thickness of each projection 504, 506 can range from about 0.075 centimeters to about 0.12 centimeters.

As can be seen in FIG. 9, the first projection 504 and the second projection 506 are axially offset from one another along the length of the body 202 of the breakable connector 500. For example, the first projection 504 and the second projection 506 can be axially offset from one another in a range of 0.75 centimeters to 0.82 centimeters along the length of the body 202 of the breakable connector 500. The first projection 504 and the second projection 506 are also circumferentially offset from one another about the B-B axis of the body 202 of the breakable connector 500. For example, the centerline 522 of the first projection 504 and the centerline 524 of the second projection 506 are circumferentially offset in a range of 105 degrees apart to 115 degrees apart.

Similar to projections 204, 206 of FIG. 2, opposing rotational forces can be applied to the projections 504, 506 in order to generate a twisting force that rotates the first portion 210 of the body 202 and the second portion 212 of the body 202 relative to one another and separates the first and second portions 210, 212 of the body 202 from one another. For example, a user can use his or her thumbs to press against each of the projections 504, 506 to apply opposing rotational forces to the projections 504, 506 and rotate the first and second portions 210, 212 of the body 202 of the breakable connector 500 relative to one another and break the frangible portion 214 of the body 202, which separates the first and second portions 210, 212 of the body 202 from one another. For example, the frangible portion 214 breaks and the first and second portions 210, 212 of the body are separated from one another when a counterclockwise rotational force in a range of 60 oz-in to 120 oz-in (0.42 N-m to 0.84 N-m) is applied to the first projection 504 and a clockwise force in a range of 60 oz-in to 120 oz-in (0.42 N-m to 0.84 N-m) is applied to the second projection 506. In some implementations, the frangible portion 214 breaks and the first and second portions 210, 212 of the body are separated from one another by applying a clockwise rotational force to the first projection 504 and applying a counterclockwise rotational force to the second projection 506.

In some implementations, user can use the projections 504, 506 to grip the breakable connector 500 and apply a bending force to the body 202 of the breakable connector 500 until the frangible portion 214 of the body 202 breaks and the first portion 210 of the body 202 separates from the second portion 212 of the body 202.

Figure 10:
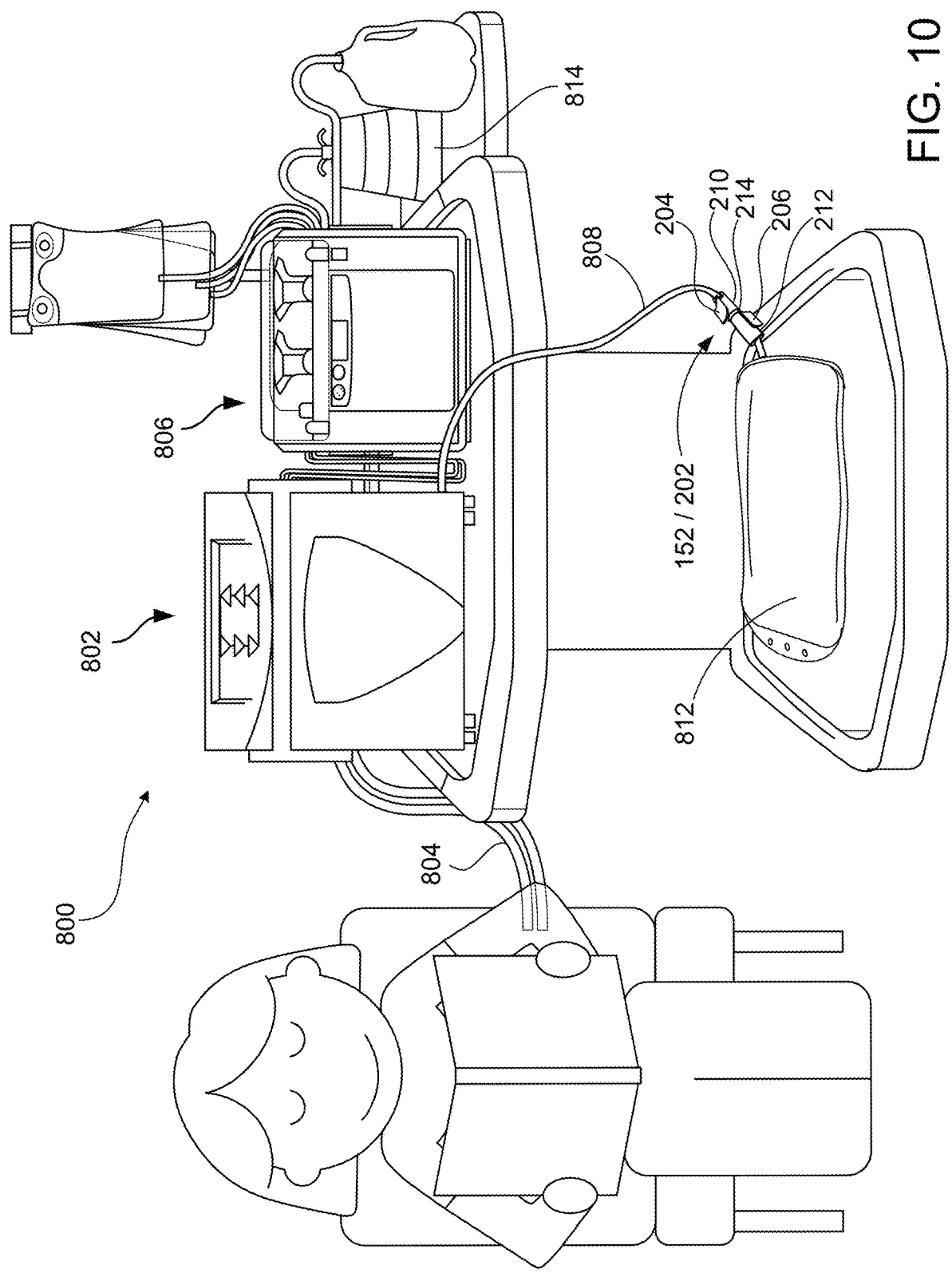
FIG. 10 is an illustration of a blood treatment system in which a drain bag is connected to a drain line by the breakable connector of FIG. 2.

While the breakable connectors 152, 154, 156, 400, 500 have been described as being used as part of a PD system, the breakable connectors can also be used in other blood treatment systems including, but not limited, hemodialysis (HD) treatment, hemofiltration (HF) treatment, and hemodiafiltration (HDF) systems. As an example, FIG. 10 depicts a blood treatment system 800 for performing one or more types of blood treatments, including HD, HF, and HDF treatments. As can be seen in FIG. 10, the blood treatment system 800 includes a blood treatment machine 802 to which a disposable blood component set 804 that forms a blood circuit is connected.

The blood treatment system 800 includes a fluid conditioning system 806 that is fluidly coupled to the blood treatment machine 802 and produces fluid, such as dialysate fluid, that can be provided to the blood treatment machine 802 and to a dialyzer connected to the blood treatment machine 802 during treatment. The blood treatment system 800 also includes a drain line 808 that is connected at a first end to a dialyzer of the blood treatment system 800 and is connected at a second end to a drain bag 812.

During treatment, arterial and venous patient lines of the disposable blood component set 804 are connected to the patient and blood is circulated through the various blood lines and components of the disposable blood component set 804. At the same time, fresh dialysate is generated by the fluid conditioning system 806 and flows from the fluid conditioning system 806 to the dialyzer of the blood treatment system 800 via fluid lines. During treatment, toxins are removed from the patient's blood and collected in the dialysate flowing through the dialyzer. The filtered blood is then returned to the patient and the spent dialysate exiting the dialyzer is flowed back to the fluid conditioning system 806. A sorbent cartridge 814 of the fluid conditioning system 806 removes (e.g., filters out) toxic substances that have collected in the spent dialysate to produce "regenerated" dialysate (e.g., cleaned, unconditioned dialysate) that flows out of the sorbent cartridge 814. The regenerated dialysate exiting the sorbent cartridge 814 is further conditioned by the fluid conditioning system 806 to meet acceptable physiological properties and is then pumped back to the blood treatment machine 802 as "fresh" dialysate.

Once treatment is complete, the spent dialysate (and any additional fluid removed from the patient) is drained from the fluid circuits of the blood treatment machine 802 and the fluid conditioning system 806 through the drain line 808 and into the drain bag 812. For example, at the end of treatment, one or more pumps of the blood treatment machine 802 and/or the fluid conditioning system 806 can be operated to draw fluid out of the fluid circuit(s) of the blood treatment machine 802 and/or the fluid conditioning system 806, through drain line 808, and into drain bag 812.

As can be seen in FIG. 10, the drain bag 812 of the blood treatment system 800 is fluidly connected to the drain line 808 using a breakable connector 152. During treatment, a portion of the spent dialysate can be sent to the drain bag 812 via the drain line 808. At the end of treatment using the blood treatment machine 802, spent dialysate flows through the drain line 808 of the system 800, through the breakable connector 152, and into the drain bag 812. Once the drain bag 812 is filled with fluid, the breakable connector 152 can be used to separate the drain bag 812 from the drain line 808, which enables a user to easily transport the drain bag 812 in order to dispose of the fluid contained within the drain bag 812.

As discussed above in reference to FIGS. 2-7, a twisting force can be applied to the body 202 of the breakable connector 152 in order to break the breakable connector 152 into two portions and separate the drain bag 812 from the drain line 808. For example, as previously discussed, applying a threshold amount of twisting force to the breakable connector 152 using a pair of projections 204, 206 extending from the body 202 of the breakable connector 152 causes a first portion 210 of the body 202 of the breakable connector 152 and a second portion 212 of the body 202 of the breakable connector 152 to rotate relative to one another and separate. Separation of the first portion 210 and second portion 212 of the body 202 of the breakable connector 152 fluidly disconnects the drain bag 812 from the blood treatment system 800 by separating an inlet of the drain bag 812 from the drain line 808 of the blood treatment system 800. In some implementations, a clamp positioned along the inlet of the drain bag 812 (such as clamps 162, 164, 166 of FIG. 1) can be closed prior to applying a twisting force to the breakable connector 152 in order to prevent fluid from leaking out of the drain bag 812 after disconnecting the drain bag 812 from the drain line 808.

As previously discussed, in some implementations, the first and second portions 210, 212 of the body 202 of the breakable connector 152 are separated from one another by applying a bending force to the breakable connector 152. For example, a user can use the projections 204, 206 to grip the breakable connector 152 with his or her fingers and apply a bending force to the body 202 of the breakable connector 152 until the frangible portion 214 of the body 202 breaks and the first portion 210 of the body 202 separates from the second portion 212 of the body 202.

While FIG. 10 depicts using a single drain bag 812 and a single breakable connector 152 during an HD, HF, or HDF treatment, in some implementations, multiple drain bags can be connected to the drain line 808 with multiple respective breakable connectors 152.

In addition, while the breakable connector 152 connecting the drain bag 812 to the drain line 808 is depicted as having wing-shaped projections 204, 206, a breakable connector 152 with other projection shapes can be used to couple the drain bag 812 to the drain line 808. For example, the breakable connector 152 can include two flat, rectangular-shaped projections coupled to the first portion 210 of the body 202 and the second portion 212 of the body, similar to projections 402, 404 in FIG. 8. In some implementations, the projections on the breakable connector 152 are two linear ribs extending along the first and second portions 210, 212 of the body of the breakable connector 152, respectively, similar to projections 504, 506 in FIG. 9.

A number of embodiments have been described. Nevertheless, it will be understood that various modifications may be made without departing from the spirit and scope of the disclosure. Accordingly, other embodiments are within the scope of the following claims.

What is claimed is:

1. A medical fluid line connector comprising:
a body defining a central opening extending therethrough, the central opening configured to fluidly connect to a medical fluid line, the body disposed along a longitudinal axis;
a first projection having a longitudinal axis parallel to the longitudinal axis of the body, the first projection extending tangentially from a first portion of the body in opposing directions from the longitudinal axis of the first projection, the first projection comprising a first surface extending outward from the longitudinal axis of the first projection and away from the first portion of the body; and
a second projection having a longitudinal axis parallel to the longitudinal axis of the body, the second projection extending tangentially from a second portion of the body in opposing directions from the longitudinal axis of the second projection, the second projection being circumferentially and axially offset from the first projection, the second projection comprising a second surface extending outwardly from the longitudinal axis of the second projection and away from the second portion of the body,
wherein the first portion of the body and second portion of the body are configured to separate from one another in response to a threshold amount of force being applied to the first projection and the second projection to rotate the first portion of the body and the second portion of the body relative to one another.

2. The medical fluid line connector of claim 1, wherein applying the threshold amount of force to the first projection and the second projection comprises simultaneously applying a counterclockwise rotational force to the first projection and a clockwise rotational force to the second projection.

3. The medical fluid line connector of claim 1, wherein:
the first portion of the body and the second portion of the body are connected by a frangible portion; and
application of the threshold amount of force to the first projection and the second projection causes the frangible portion to break.

4. The medical fluid line connector of claim 3, wherein a thickness of the frangible portion is smaller than a thickness of the first portion of the body or a thickness of the second portion of the body.

5. The medical fluid line connector of claim 1, wherein the first projection comprises a first curved wing, and the first surface comprises a first curved surface.

6. The medical fluid line connector of claim 5, wherein the second projection comprises a second curved wing, and the second surface comprises a second curved surface.

7. The medical fluid line connector of claim 6, wherein the first curved surface of the first curved wing and the second curved surface of the second curved wing are each sized to accommodate an adult thumb.

8. The medical fluid line connector of claim 6, wherein the first curved wing and the second curved wing are each configured to receive the threshold amount of force without the first curved wing or the second curved wing separating from the body.

9. The medical fluid line connector of claim 1, wherein the first surface of the first projection comprises a first flat, rectangular surface.

10. The medical fluid line connector of claim 9, wherein the second surface of the second projection comprises a second flat, rectangular surface.

11. The medical fluid line connector of claim 1, wherein:
the first projection is connected to the first portion of the body at a first location on the first portion of the body,
the second projection is connected to the second portion of the body at a second location in the second portion of the body, and
the first location is circumferentially spaced apart from the second location by 105 degrees to 115 degrees.

12. The medical fluid line connector of claim 1, wherein:
the first projection is integrally molded with the first portion of the body; and
the second projection is integrally molded with the second portion of the body.

13. The medical fluid line connector of claim 1, wherein the first and second projections are discrete components that are coupled to the first and second portions, respectively, of the body.

14. A method of disconnecting a fluid bag from a fluid line, the method comprising:
applying a counterclockwise rotational force to a first projection extending tangential from a first portion of a body of a connector in opposing directions from a longitudinal axis of the first projection, the longitudinal axis of the first projection being parallel to a longitudinal axis of the body, wherein the connector is fluidly coupled to the fluid line and an inlet of the fluid bag, the first projection comprises a first surface extending outward from the longitudinal axis of the first projection and away from the first portion of the body; and
simultaneously applying a clockwise rotational force to a second projection extending tangentially from a second portion of the body of the connector in opposing direction from a longitudinal axis of the second projection, the longitudinal axis of the second projection being parallel to the longitudinal axis of the body, the second portion of the body being axially offset from the first portion of the body, the second projection comprising a second surface extending outward from the longitudinal axis of the second projection and away from the second portion of the body,
wherein simultaneously applying the counterclockwise rotational force to the first projection and the clockwise rotational force to the second projection generates a twisting force sufficient to separate the first portion of the body from the second portion of the body.

15. The method of claim 14, wherein simultaneously applying the counterclockwise rotational force to the first projection and the clockwise rotational force to the second projection causes a frangible portion of the body of the connector to break.

16. The method of claim 14, further comprising closing a clamp positioned along the fluid line or along the inlet of the fluid bag.

17. The method of claim 14, wherein the counterclockwise rotational force is in a range of 60 oz-in to 120 oz-in and the clockwise rotational force is in a range of 60 oz-in to 120 oz-in.

18. The method of claim 14, wherein the twisting force is a force that exceeds 60 oz-in.

19. The method of claim 14, wherein the first projection is a first curved wing and the second projection is a second curved wing, the first surface comprising a first curved surface and the second surface comprising a second curved surface.

20. The method of claim 14, wherein:
applying the counterclockwise rotational force to the first projection comprises using a first thumb to push against the first projection in a first direction; and
applying the clockwise rotational force to the second projection comprises using a second thumb to push against the second projection in a second direction opposite the first direction.

21. A system comprising:
a medical treatment device;
a fluid bag;
a fluid line configured to be secured to the medical treatment device and fluidly coupled to the fluid bag; and
a connector configured to fluidly couple the fluid bag to the fluid line, the connector comprising:
a body defining a central opening extending therethrough, the body disposed along a longitudinal axis;
a first projection having a longitudinal axis parallel to the longitudinal axis of the body, the first projection extending tangentially from a first portion of the body in opposing directions from the longitudinal axis of the first projection, the first projection comprising a first surface extending outward from the longitudinal axis of the first projection and away from the first portion of the body; and
a second projection having a longitudinal axis parallel to the longitudinal axis of the body, the second projection extending tangentially from a second portion of the body in opposing directions from the longitudinal axis of the second projection, the second projection being axially and circumferentially offset from the first projection, the second projection comprising a second surface extending outward from the longitudinal axis of the second projection and away from the second portion of the body, wherein the first portion of the body and the second portion of the body are configured to separate from one another in response to a threshold amount of force being applied to the first projection and the second projection to generate a twisting force that rotates the first portion of the body and second portion of the body relative to one another.

22. The system of claim 21, further comprising:
a second fluid bag; and
a second connector configured to fluidly couple the second fluid bag to the fluid line.

23. The system of claim 21, wherein:
the first projection comprises a first curved wing, and the first surface comprises a first curved surface; and
the second projection comprises a second curved wing, and the second surface comprises a second curved surface.

24. The medical fluid line connector of claim 11, wherein:
the first location is radially aligned with the longitudinal axis of the first projection, and the second location is radially aligned with the longitudinal axis of the second projection.

25. The medical fluid line connector of claim 1, wherein a length of the first projection along the longitudinal axis of the first projection is greater than a thickness of the first projection along a radial direction from the longitudinal axis of the body through the longitudinal axis of the first projection.

26. The medical fluid line connector of claim 25, wherein a length of the second projection along the longitudinal axis of the second projection is greater than a thickness of the second projection along a radial direction from the longitudinal axis of the body through the longitudinal axis of the second projection.

27. The medical fluid line connector of claim 1, wherein the longitudinal axis of the first projection is a centerline of the first projection, and the longitudinal axis of the second projection is a centerline of the second projection.

\* \* \* \* \*